United States Patent

Mayer

Patent Number: 5,820,753
Date of Patent: Oct. 13, 1998

[54] DISPOSABLE DENTAL EVACUATION TRAP

[75] Inventor: Stanley E. Mayer, Bronx, N.Y.

[73] Assignee: Coltene/Whaledent, Inc., Mahwah, N.J.

[21] Appl. No.: 786,244

[22] Filed: Jan. 21, 1997

[51] Int. Cl.$^6$ .......................... B01D 29/00; B01D 27/08; A61C 17/06

[52] U.S. Cl. .......................... 210/232; 210/167; 210/238; 210/406; 210/416.1; 210/497.01; 210/499; 210/470; 210/471; 210/474; 210/493.1; 210/435; 210/441; 433/92; 433/97

[58] Field of Search ..................... 210/167, 232, 210/237, 238, 406, 416.1, 470, 471, 472, 473, 474, 493.1, 497.01, 499, 435, 441, 444; 433/92, 97

[56] References Cited

U.S. PATENT DOCUMENTS

| | | |
|---|---|---|
| 3,542,201 | 11/1970 | Belonger et al. . |
| 4,154,679 | 5/1979 | Farage ..................... 210/169 |
| 4,169,059 | 9/1979 | Storms . |
| 5,407,565 | 4/1995 | Austin, Jr. ................. 210/188 |
| 5,567,323 | 10/1996 | Harrison, Jr. ............. 210/251 |
| 5,571,412 | 11/1996 | Nerli ....................... 210/232 |

*Primary Examiner*—Robert Popovics
*Attorney, Agent, or Firm*—Helfgott & Karas, P.C.

[57] ABSTRACT

Undesired contact with dental debris is minimized by a disposable dental trap which is provided with a removable top cover and a pivotable handle. The useful capacity of the trap is increased with a corrugated filter which increases the available filter surface area and thereby reduces the frequency of trap replacement.

13 Claims, 3 Drawing Sheets

DISPOSABLE DENTAL EVACUATION TRAP

BACKGROUND OF THE INVENTION

1. Field of the Invention

The present invention relates in general to a filter assembly for trapping solid debris evacuated from the mouth of a dental patient and relates in particular to such a filter which includes a substantially closed container provided with a handle for minimizing or eliminating contact with the filtered contents.

2. Description of Prior Developments

A tubular instrument is typically placed within a patient's mouth during various dental procedures as a source of vacuum, such as a vacuum pump, draws the solid and liquid debris from the patient's mouth through the instrument into a filter or trap via a flexible hose. Conventional filters included a mesh or screen which trapped solid particles and prevented them from entering the suction pump where they could cause damage.

Although prior dental traps have, in general, performed satisfactorily, such designs have typically taken the form of open topped cylindrical cups having generally flat perforated floors. A drawback associated with such open-topped designs is the possibility of contact between the contents of the trap and one's clothing or skin when replacing the trap.

With the increased health risks associated with bodily contact with hazardous waste and contaminants of the type found in dental traps, it has become increasingly important to avoid all contact with the solid debris, sludge and slime which collects within such traps.

A drawback associated with certain prior dental traps is the use of a relatively flat mesh or screen for collecting debris. Such flat surfaces become clogged rather quickly and require relatively frequent replacement. It can be appreciated that, as the capacity of a dental trap increases, its frequency of replacement is reduced.

Accordingly, a need exists for a dental trap which has a high volume capacity for the retention of a large volume of debris. Such a trap requires infrequent replacement and thereby reduces the opportunity for contact of its contents with skin or clothing.

Another need exists for a dental trap which minimizes or eliminates the possibility of contact between the contents of the trap and one's skin or clothing regardless of the frequency of trap replacement.

Still another need exists for a dental trap which is not only easy to remove and replace but which can be removed and replaced without any dripping or splashing of its contents.

Various other objects, advantages and features of the present invention will become readily apparent from the ensuing detailed description and the novel features which will be particularly pointed out in the appended claims.

SUMMARY OF THE INVENTION

The present invention has been developed to fulfill the needs noted above and therefore has as an object the provision of a dental trap which includes a high capacity, high volume trap chamber which extends the useful life of the trap and thereby reduces the opportunity for contact with the trap contents.

Another object of the invention is to provide a dental trap which prevents contact between the debris retained within the trap and an operator's skin and clothing, as well as any surrounding surfaces.

A further object of the invention is to provide a dental trap which is easy to remove and which provides a gripping surface which is remote from and protected from contact with the contents of the trap.

These and other objects are met by the present invention which includes a generally cylindrical trap having a corrugated bottom. The corrugations in the bottom of the trap are perforated for allowing the passage of fluids while retaining solid and semi-solid debris within the trap. Because the floor of the trap is corrugated, its surface area is increased significantly over that of flat-floored prior art traps and can continue functioning long after conventional traps become clogged.

The trap further includes a flexible handle which facilitates the removal and replacement of the trap and provides a gripping surface which is protected from exposure to the contents of the trap.

A generally disk-shaped cover is provided for tightly fitting over the open top of the trap. A slit is provided in the cover for allowing the passage of the handle which extends upwardly through the cover. Recesses are provided in the top of the cover for allowing the handle to be folded over and maintained within the recesses during operation.

The aforementioned objects, features and advantages of the invention will, in part, be pointed out with particularity, and will, in part, become obvious from the following more detailed description of the invention, taken in conjunction with the accompanying drawings, which form an integral part thereof.

BRIEF DESCRIPTION OF THE DRAWINGS

In the drawings.

In the various figures of the drawings, like reference characters designate like parts.

DETAILED DESCRIPTION OF THE PREFERRED EMBODIMENTS

Figure 1:
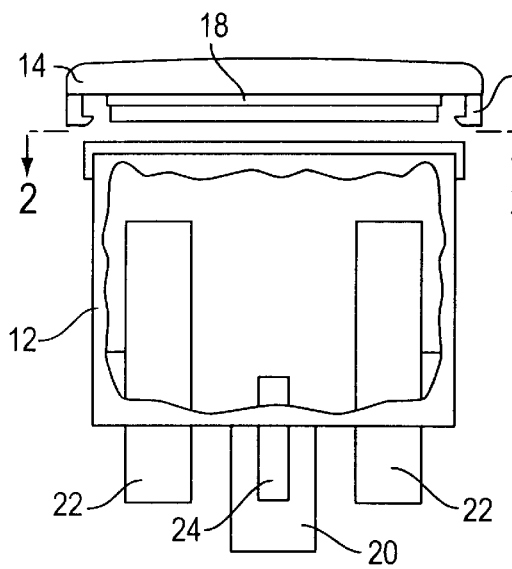
FIG. 1 is an exploded schematic front elevation view, partly in section, showing a collecting chamber of the type connected between a suction source and a dental evacuator according to the prior art.
Figure 2:
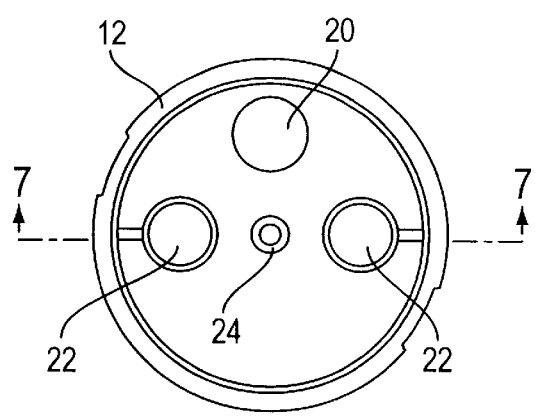
FIG. 2 is a top plan view of the collector of FIG. 1 taken along section line 2—2 thereof.
Figure 3:
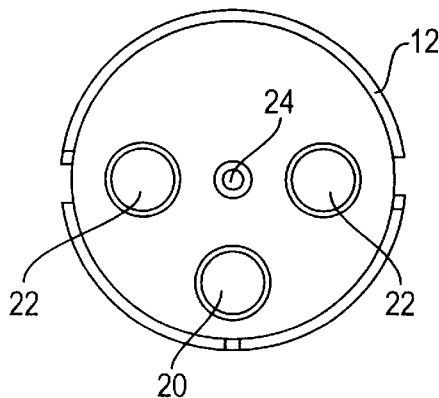
FIG. 3 is a bottom view of FIG. 1.

In order to better appreciate the advantages and features of the present invention, a brief review of the prior art of FIGS. 1 through 6 is provided. As seen in FIG. 1, a solids collector 10 includes a generally hollow cylindrical canister 12 and a removable lid 14. Lid 14 is attached to canister 12 via bayonet connectors 16. O-ring 18 provides a fluid tight seal between the canister and lid.

The solids collector 10 is typically mounted within a part of the chair side evacuation equipment found in most dental offices. An evacuation system powered by a vacuum pump is provided for evacuating saliva and other debris from the mouth of a patient. More particularly, a tube from the suction pump is connected to a large vacuum fitting 20 which freely communicates with the interior of the canister 12.

Suction from within the canister is delivered to one or more instruments which a dentist may selectively position within a patient's mouth. These instruments are interconnected to the interior of canister 12 via one or more high volume suction fittings 22 or a low volume suction fitting 24. Fittings not in use are typically plugged. A flexible tube is interconnected between one or more of the suction fittings 22,24 and the evacuation instrument manipulated by the dentist.

Figure 4:
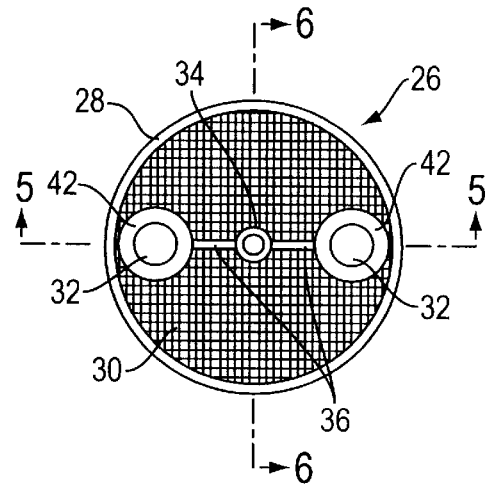
FIG. 4 is a top plan view of a dental trap according to the prior art.
Figure 5:
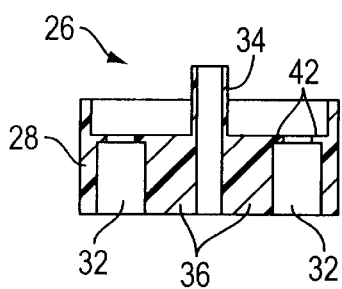
FIG. 5 is a central sectional view taken through line 5—5 of FIG. 4.
Figure 6:
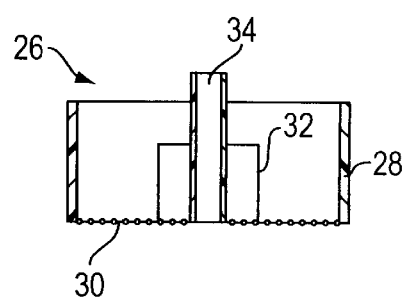
FIG. 6 is a central sectional view taken through line 6—6 of FIG. 4.
Figure 7:
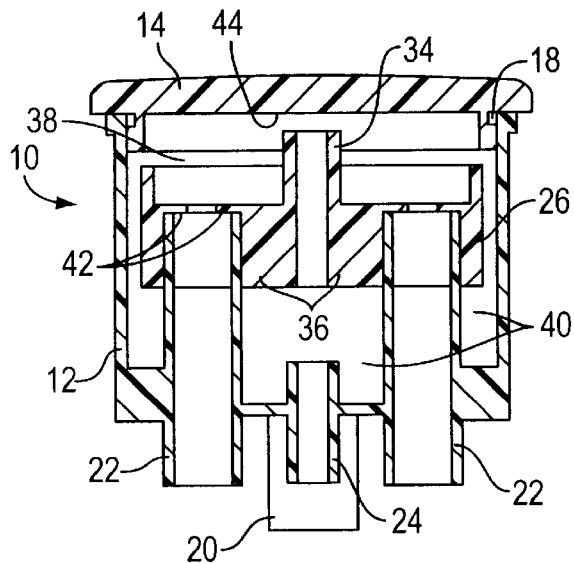
FIG. 7 is a central sectional view taken along section line 7—7 of FIG. 2 and showing the trap of FIG. 5 seated therein.
Figure 8:
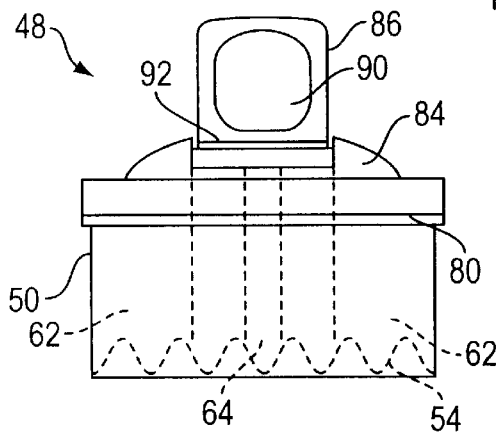
FIG. 8 is a front elevation view of a dental trap constructed in accordance with the present invention.

In order to prevent solid particles from entering the vacuum pump through fitting 20, a filter 26 as shown in FIGS. 4 through 6 is mounted within canister 12, as shown in FIG. 7. Filter 26 includes a cylindrical side wall 28 and a floor or bottom 30 formed as a screen or mesh. A pair of cylindrical pipes 32 extends upwardly from the screen floor 30 and is positioned so as to freely slide over the pair of high volume suction fittings 22 provided within canister 12. A smaller diameter cylindrical pipe 34 rises upwardly from the center of floor 30 and, when mounted within canister 12, is aligned generally coaxially with the low volume suction fitting 24. A strengthening rib 36 may extend from the central cylindrical pipe 34 to each larger cylindrical pipe 32.

As seen in FIG. 7, when the filter 26 is mounted in the solids collector 10, the filter serves as an interface or a strainer for separating solids and semi-solids from the fluids passing through the solids collector. That is, solid and fluid particles which enter the canister through either the high volume suction fittings 22 or the low volume suction fitting 24 are drawn into the upper chamber 38 of the canister via pipes 32 or 34. The evacuated material is then drawn against the mesh floor 30 of the filter 26.

Solids are caught and retained within mesh 30. Fluids pass through the mesh into the lower chamber 40 and are drawn out of chamber 40 and out of canister 12 via the large vacuum fitting 20. It should be noted that overhanging flanges 42 hold the filter 26 in a predetermined position atop the high volume suction fittings 22.

After a relatively short period of use, the screen or mesh floor 30 in the filter 26 becomes clogged and requires replacement. At this time, the lid 14 is removed from the canister 12 for allowing access to the filter 26. Even before the filter is removed, a potential contamination problem exists insofar as the underside 44 of lid 14 has been exposed to the interior of the canister. Lid 14 can thus pose a health risk in addition to the filter 26.

After the lid 14 has been removed, the cylindrical pipe 34 on filter 26 is typically grabbed or pinched and pulled upwardly thereby unseating the filter 26 from the high volume suction fittings 22. This is generally a very unpleasant task insofar as the contents caught and held by the screen floor 30 are generally offensive and potentially laden with bacteria, virus and other noxious substances.

In order to reduce the possibility of contamination during the installation and removal of the filter 26 noted above, and to increase the capacity of such a filter, the dental trap assembly 48 as shown in FIGS. 8 through 16 has been developed in accordance with the present invention. The trap assembly 48 includes a cup-shaped container 50 having an upstanding, generally cylindrical side wall 52. The floor of the container is formed as a perforated corrugated filter 54. Filter 54 includes a uniform pattern or matrix of generally rectangular shaped or square shaped perforations 56. The corrugated filter 54 along with side wall 52 is advantageously injection molded as a single homogeneous integral assembly from a plastic material such as polyethylene.

Figure 9:
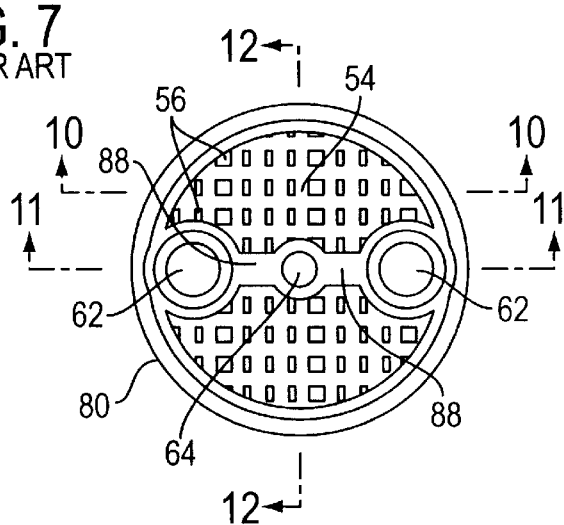
FIG. 9 is a bottom view of FIG. 8.
Figure 10:
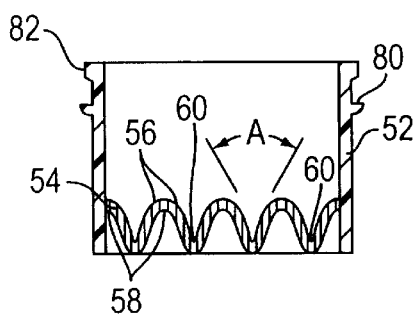
FIG. 10 is a view in section taken along section line 10—10 of FIG. 9 with the container cover removed.
Figure 11:
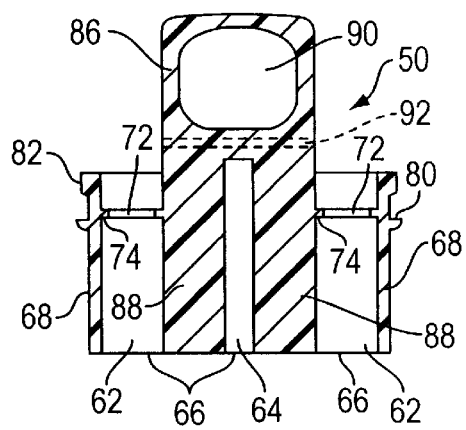
FIG. 11 is a central sectional view taken along line 11—11 of FIG. 9.

The corrugated filter 54 includes a series of crests 58 and troughs 60 which are arranged in a generally undulating sinusoidal or saw tooth pattern. In one embodiment, the included angle A defined between a pair of diverging trough walls may be set at approximately sixty degrees as shown in FIG. 10. As seen in FIGS. 9 and 11, the container 50 also includes a pair of vacuum conduits 62 which serve the same purpose as the large cylindrical pipes 32 noted above with respect to the prior art.

Container 50 also includes a low volume vacuum conduit 64 located in the center of the container 50. Each vacuum conduit 62,64 includes an evacuation port 66 which extends through the filter 54 and defines the entry point of vacuum applied to the filter 48. Each high volume vacuum conduit 62 includes a tubular wall 68 and the low volume vacuum conduit 64 includes a tubular wall 70 (FIG. 12).

Figure 16:
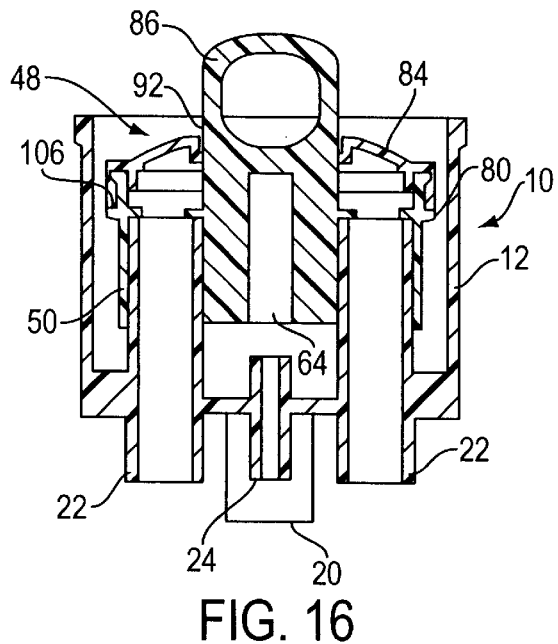
FIG. 16 is a central sectional view of the trap of FIG. 8 mounted in the collector of FIG. 1.

As seen in FIG. 11, each side wall 68 leads upwardly to a high volume suction port 72 bordered by an overhanging annular ridge 74. Ridge 74 serves to position and locate the container 50 within the solids collector 10 as shown in FIG. 16 in the manner noted above with respect to the prior art.

Figure 12:
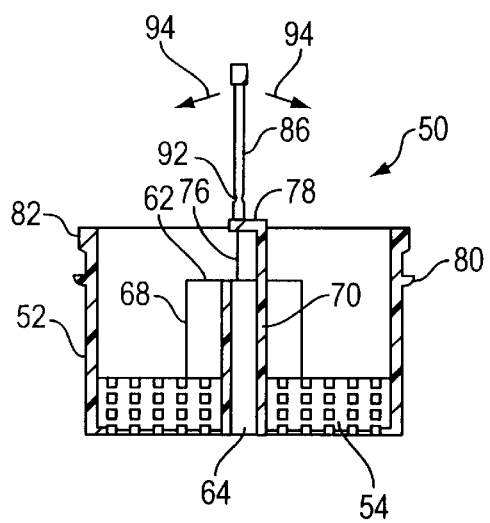
FIG. 12 is a central sectional view taken through line 12—12 of FIG. 9.

As seen in FIG. 12, the tubular wall 70 of the low volume vacuum conduit 64 leads upwardly to an axially-extending evacuation port 76. Port 76 takes the shape of a ninety degree to two hundred and seventy degree segment of a cylinder with end wall 78 extending transversely over the upper end of the low volume conduit 64. This particular configuration of evacuation port 76 extends over a one hundred and eighty degree opening and is highly resistant to clogging which can be a problem with small diameter conduits such as conduit 64.

As further seen in FIGS. 8 through 12, the upper end portion of the cylindrical side wall 52 is formed with an annular ridge 80 for locating the lower edge of a cover or cap 84 discussed further below. The upper edge of side wall 52 terminates in an outwardly projecting annular lip 82 for forming a locking bead with cover or cap 84 shown in FIGS. 8 and 13 through 16. It should be appreciated that other types of snap fit or other securing arrangements could be used.

A handle 86 extends upwardly through the open top of the container 50. Handle 86 may be formed as an extension of side braces 88 which extend between and mutually support the central low volume vacuum conduit 64 and the two diametrically-opposed high volume conduits 62.

Handle 86 may include a central aperture 90 and a reduced material section 92 located above the low volume evacuation port 76 and below the central aperture 90. The reduced material section 92 as best seen in FIG. 12 provides a pivot line about which the handle 86 may be folded or pivoted in the direction of arrows 94. As further seen in FIG. 12, the entire canister 12 including the side wall 52, filter 54, high and low volume conduits 62,64, braces 88, and handle 86 may be simultaneously and homogeneously molded during a single injection molding operation using a suitable plastic such as polyethylene.

Figure 13:
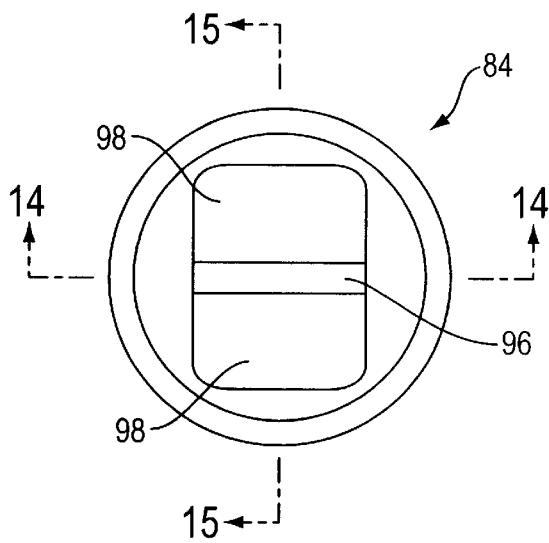
FIG. 13 is a top plan view of the cap of FIG. 8.
Figure 14:
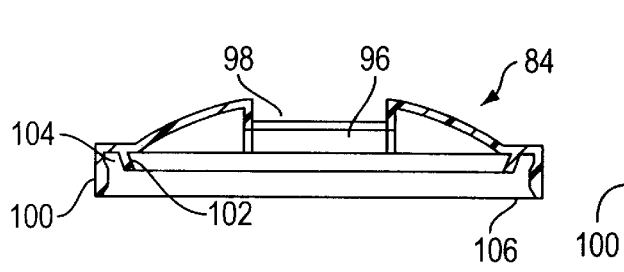
FIG. 14 is a sectional view taken along line 14—14 of FIG. 13.
Figure 15:
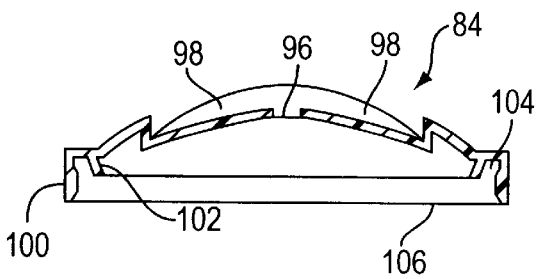
FIG. 15 is a central sectional view taken through section line 15—15 of FIG. 13.

Details of the cover or cap 84 are shown in FIGS. 13 through 15 wherein the cap 84 is shown with a central slot or aperture 96 formed therethrough for allowing handle 86 to pass upwardly through the cover 84. A pair of recesses 98,98 is configured as generally rectangular adjoining pockets positioned adjacent each edge of the central slot 96. Each recess 98 is configured to compliment the shape of the upper pivotal end of handle 86 so as to form a nest for receiving the handle when it is folded over and against the surface or floor of one of the recesses 98.

Cover or cap 84 further includes an annular side rim 100 which, together with an annular resilient retaining flange 102, define an annular undercut pocket 104 for receiving with a press fit or snap fit the annular lip 82 formed on the upper end of the cylindrical side wall 52 of container 50. This snap over fit is best seen in cross section in FIG. 16.

As further seen in FIG. 16, when the cover 84 is press fit and snapped over the container 50, the lower edge 106 of the side rim 100 is positively located on the annular ridge 80 of the side wall 52. As heretofore mentioned, other securing arrangements could be utilized. It can be appreciated that, because the cap extends completely over the container 50 as well as over the corrugated filter 54, removal of the entire dental trap assembly 48 out of the solids collector 10 can be accomplished without any splashing or contamination. Moreover, because of the protection afforded by cover 84, the contamination problem on the under side 44 of lid 14 as shown in FIG. 7 is virtually eliminated since contaminants cannot splash through the top of the cover 84 and contact the lid 14.

Although the handle 86 may be attached directly to cover 84 rather than to container 50, it has been found advantageous to connect the handle to the container since an upward pull on handle 86 will tend to lift the container rather than tend to pull the cover off of the container as would be the case if the handle was directly connected to the cover. Even though the handle 86 is shown projecting above the canister 12 in FIG. 16, once the lid 14 is applied and connected to canister 12, the handle 86 is forced down into one of the recesses 98 as the handle pivots about the pivot line or pivot portion 92. When the movable lid is subsequently removed from the solids collector 10, the resilient plastic material of handle 86 causes the handle to pop upwardly as shown in FIG. 16 thereby providing easy access to the dental trap assembly 48 for facilitating its removal.

It can now be appreciated that, by providing handle 86 on the dental trap 48, one need not grip a contaminated or slimy surface such as is the case with cylindrical pipe 34 in the prior art. Moreover, by completely covering the interior of container 50, any fluids or other contaminants contained within the container 50 will be prevented from spilling out of the top of the container thereby avoiding contamination of clothing, dental equipment, floors, counters, and any other surrounding surfaces including the skin of dental personnel.

Because the filter is corrugated, it provides a greater filter area, i.e. forty percent greater than flat filter surfaces. This translates into less frequent replacement and less likelihood of contamination. Since the injection molded cover 84 is press fit or snapped on the container 50, any collected sludge or slime will not splash out of the container upon its removal from the evacuation system.

Obviously, numerous modifications and variations of the present invention are possible in the light of the above teachings. It is therefore to be understood that within the scope of the appended claims, the invention may be practiced otherwise than as specifically described herein.

What is claimed is:

1. A dental trap comprising a container constructed and arranged for use with a dental evacuation system, said container defining a bottom wall comprising a filter defining a series of perforated crests and troughs for trapping dental debris within said trap, a vacuum conduit defining an evacuation port extending through said filter, a suction port disposed within said container, a tubular wall extending between said evacuation port and said suction port and an end wall extending transversely over said vacuum conduit adjacent said suction port.

2. The trap of claim 1, wherein said filter comprises an injection molded filter formed on said container.

3. The trap of claim 1, wherein said container further comprises a handle for installing and removing said trap from said dental evacuation system.

4. The trap of claim 1, further comprising a cover extending over said filter.

5. The trap of claim 1, wherein said vacuum conduit comprises a tubular side wall and an end wall and wherein an axially-extending suction port is formed in said side wall adjacent said end wall.

6. The trap of claim 1, further comprising a removable cover fitted on said container and a handle provided on said container, said cover having an aperture formed therethrough and said handle extending through said aperture.

7. The trap of claim 6, wherein said cover comprises a recess for receiving said handle.

8. A disposable dental trap comprising:

a container comprising an integral filter defining a bottom wall of said container and a vacuum port extending through said integral filter constructed and arranged for fluid communication with a dental evacuation system, said integral filter defining a series of perforated crests and troughs for trapping dental debris; and a cap connected directly to said container for preventing escape of dental debris during removal of said trap from said evacuation system.

9. The trap of claim 8, wherein said cap is press fit on said container.

10. The trap of claim 8, further comprising a handle extending from said cap.

11. The trap of claim 10, wherein said handle comprises a pivot portion for pivoting said handle against said cap.

12. The trap of claim 11, wherein said cap comprises a recess for receiving said handle when said handle is pivoted against said cap.

13. The trap of claim 8, wherein said container comprises a handle and said cap comprises a slot and wherein said handle extends through said slot.

\* \* \* \* \*